United States Patent [19]

Eigen et al.

[11] 4,349,534
[45] Sep. 14, 1982

[54] DENTIFRICE COMPOSITION

[75] Inventors: Edward Eigen, East Brunswick; Dina I. Brachman, Highland Park, both of N.J.

[73] Assignee: Colgate-Palmolive Company, New York, N.Y.

[21] Appl. No.: 321,871

[22] Filed: Nov. 16, 1981

[51] Int. Cl.³ .................... A61K 7/16; A61K 7/18; A61K 7/26
[52] U.S. Cl. ...................... 424/52; 424/49; 424/57; 424/58
[58] Field of Search .................... 424/49–58

[56] References Cited

U.S. PATENT DOCUMENTS

| | | | |
|---|---|---|---|
| 1,275,779 | 8/1918 | Spies et al. | 424/49 |
| 1,522,410 | 1/1925 | Bluhm et al. | 424/58 |
| 1,527,523 | 2/1925 | Nitardy et al. | 424/58 |
| 1,565,864 | 12/1925 | Putt | 424/49 |
| 1,591,727 | 7/1926 | Nitardy | 424/49 |
| 1,664,182 | 3/1928 | Parisi | 424/58 |
| 2,436,818 | 3/1948 | Musher | 424/47 |
| 4,217,341 | 8/1980 | Suddick et al. | 424/58 |

FOREIGN PATENT DOCUMENTS

| | | | |
|---|---|---|---|
| 810292 | 8/1951 | Fed. Rep. of Germany | 424/58 |
| 2143622 | 2/1973 | France | 424/58 |
| 52-6345 | 2/1977 | Japan | 424/58 |

OTHER PUBLICATIONS

McClure, Arch. Oral Biol. 9: 219–221, (1964), "Inhibition of Experimental Caries by Oat Hulls".
Madsen, et al., J. Dent. Res. 41: 405–412, (1962), "Effect of Rice Hulls and Other Seed Hulls on Dental Caries Production in the Cotton Rat".
Madsen, et al. J. Dent. Res. 42: 137–143, (1963), "Prolonged Effect on Caries of Short-Term Feeding of Rice Hulls to Cotton Rat".
Taketa, et al., J. Am. Dietetic Assn. 33: 575–578, (1957), "Oat Hull Fractions and the Development of Dental Caries".
Vogel, et al., J. Dent. Res. 41: 707–712, (1952), Studies on Anti cariogenic Activity of Oat Hulls.
Science News Letter, Apr. 19, 1958, p. 244, Oat Hull Extract Protects Teeth.

*Primary Examiner*—Shep K. Rose
*Attorney, Agent, or Firm*—Robert L. Stone; Murray M. Grill; Herbert S. Sylvester

[57] ABSTRACT

A novel dentifrice composition containing rice hulls ground to a particle fineness which passes a 200 mesh sieve, preferably passes a 325 mesh sieve, as the essential abrasive in amounts less than 40% by weight of the total composition.

10 Claims, No Drawings

DENTIFRICE COMPOSITION

This invention relates to a stable dentifrice comprising ground rice hulls, the particles of which pass a 200 mesh sieve, as the essential dental abrasive, the total amount of abrasive consitituting less than 40% by weight of the composition.

BACKGROUND AND PRIOR ART

Rice hulls, a byproduct in the preparation of rice grains, has found many uses. One particular use is as a cleaning scouring abrasive in mechanics' handsoaps, wherein the rice hulls are ground to pass 20 but not 100 mesh, in amounts of 10 to 25% by weight of the soap composition, as disclosed in chapter 12 page 331 of *Rice Chemistry and Technology*, Edited by D. F. Houston, published by American Association of Cereal Chemists, Inc., St. Paul, Minn., 1972. Another use for finely ground hulls, described on page 332 of this same book, is as a filler in plastics and plywood glues. Still another use is as a carrier or adsorbent for materials ranging from vitamins to pesticides to explosives. However, there is no disclosure of the use of finely ground rice hulls as an abrasive in dentifrice compositions.

The prior art also discloses the use of cereal meal or soybean meal in dentifrice formulations as shown in U.S. Pat. No. 2,154,168; comminuted vegetable substances (cereal) such as rice, maize or corn is disclosed in U.S. Pat. No. 1,693,349; and a mixture of powdered rice, beans and bones is disclosed in U.S. Pat. No. 1,664,182. Natural fibers such as orris root, arrow root and vegetable fiber in dentifrices is disclosed in U.S. Pat. No. 1,523,840, No. 1,529,486 and No. 1,522,410. U.S. Pat. No. 2,436,818 also discloses the use of small amounts of a particular fraction of dehulled oats as a beneficial ingredient in dentifrices.

Although the prior art discloses natural products as an ingredient in dentifrices, said products do not include rice hulls, a byproduct in the preparation of rice grains. More specifically, rice grains are obtained by first dehulling and then debranning the rice product. It is the rice hulls that are the subject matter of this invention.

SUMMARY OF THE INVENTION

The primary object of the invention is to provide a dentifrice formulation having excellent cleaning and stain removal properties comprising finely divided rice hulls ground to pass a 200 mesh sieve, as the dental abrasive. All references to sieves herein are to U.S. Sieve Series.

Another object of this invention is to provide a dentifrice formulation of suitable consistency containing less than 40% ground rice hull abrasive.

Still another object of this invention is to provide a dentifrice having anticaries properties by utilizing ground rice hulls as the abrasive ingredient.

Another object of this invention is to provide a stable dentifrice comprising a fluorine-containing compound such as monofluorophosphate, by utilizing finely divided rice hulls ground to pass a 200 mesh sieve, as the abrasive ingredient.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the dentifrice of this invention comprises, as the dental abrasive, ground rice hull particles capable of passing a 200 mesh sieve.

More specifically, present invention relates to a stable dentifrice comprising less than 40% ground rice hulls the particles of which pass a 200 mesh sieve as the sole dental abrasive. Other dental abrasives may be substituted for part of the ground rice hulls in amounts of less than 50% of the total abrasive content, and less than the ground rice hull content. The dentifrice may also contain a fluorine-containing compound which is stabilized by the ground rice hulls.

It has been unexpectedly found that ground rice hulls particles which pass a 200 mesh sieve can be used as a dental abrasive in lesser amounts than conventional abrasives to obtain a dentifrice of suitable consistency and of superior cleaning and stain removal properties. A content of 32% ground rice hulls is at least as effective as a 50% content of conventional abrasives, and in many instances more effective. It has additionally been found that fluorine-containing compounds added to the formulation are stabilized by the ground rice hulls. Another advantage in using rice hulls is the reported anti-caries factor found therein when used as a feed in cariogenic diets to rats and hamsters, as reported in *Cereal Foods World* January 1981, Vol. 26, No. 1, pages 19-25. Still another advantage of using rice hulls is that it is a natural abrasive. All these attributes makes it an excellent substitute for conventional dental abrasives presently on the market.

It is essential that the rice hulls be ground to a particle size so that all particles pass a 200 mesh sieve (74 microns), and preferably a 270 mesh sieve (53 microns), and most preferably a 325 sieve (44 microns). The particle size distribution is most preferably about 2 to 40 microns with an average median size of about 11.5 to 19 microns. Particles which do not pass a 200 mesh sieve are not useful as dental cleaners, and also adversely affect the consistency of the dentifrice. The rice hulls may be utilized provided the particles pass through a 200 mesh sieve screen.

Rice hulls have a hardness value of 5.5-6.5 on the Moh scale, which is within the range of abrasives heretofore used in dentifrices, and less than of tooth enamel which has a value of 7. The composition of rice hulls is about 34 to 44% cellulose, 16 to 22% pentosans, 13 to 29% ash (silica), 31 to 50% crude fiber (lignin), 24 to 39% nitrogen free extract, 0.4 to 3% crude fat, 1.7 to 7.3% crude protein and 2.4 to 11% water (page 308 of aforecited *Rice* text). Rice hulls are obtained unbleached and are generally used as such, although if desired they could be bleached.

It has been found that a 50% suspension of ground rice hulls which pass a 200 mesh sieve in a sodium carboxymethyl cellulose gel has abrasivity similar to a commercial toothpaste containing 50% hydrated alumina, hydrated silica and dicalcium phosphate as abrasive. The RDA (radioactive dentine abrasivity) value of ground rice hulls was determined by utilizing a 62.5 ml of a 1% Na carboxymethyl cellulose solution containing 12.5 g ground rice hulls with the following results:

| Rice Hulls | RDA |
|---|---|
| 200-270 mesh | 270 |
| Less than 325 mesh | 259 |
| 270-325 mesh | 230 |

The RDA values are within the preferred range of 200 to 450 for a suitable dentifrice.

The RDA values are obtained by a procedure based on a radioactive technique described in the literature: Stookey, C. K. and Muhler, J. C., *J. Dental Research* 47, 524–538 (1968).

The results of Stain Removal (SR) tests on toothpastes containing 32% ground rice hulls of less than 325 mesh particle size, compared favorably to aforesaid commercial toothpaste, an SR value of 32% compared to an SR value of 22% respectively.

In a stain removal test, sections of human dental enamel are etched with 0.1 N HCl for 2 minutes, rinsed with water, then wet with a dilute solution of stannous fluoride, wiped dry, and finally exposed to a stream of hydrogen sulfide gas which results in the deposition of a brown deposit of stannous sulfide. The amount of stain on the surface is measured with a Gardner Automatic Color Difference meter. The surface is then brushed with a mechanical brushing machine for 3000 reciprocal strokes with a slurry of a dentifrice, and the residual stain measured with the meter. Finally, the stain which remains is completely removed with dental pumice and the reflectance of this surface is read. The ability of a dentifrice to remove the stain is expressed by the following equation.

$$\text{Percent Stain removed} = \frac{(Rd\ 3000\ \text{strokes} - Rd\ \text{initial})\ 100}{Rd\ \text{pumiced} - Rd\ \text{initial}}$$

where Rd initial, Rd 3000 strokes, and Rd pumiced are respectively the reflectance values measured on the initially stained surface, after brushing for 3000 reciprocal strokes and after removing the residual stain by pumicing.

It has additionally been found that fluorine-containing compounds such as monofluorophosphate are stabilized in rice hull dentifrice formulations for at least 9 weeks at 120° F. The results of aging tests on a ground rice hull dentifrice containing monofluorophosphate (MFP), determined by F solubility, are shown in the following table:

TABLE 1

| Time | Temp. (F.) | Total soluble F | Ionic F (ppm) | Sol. MFP |
|---|---|---|---|---|
| Initial | | 0.092 | 37 | 0.088 |
| 2 wk | 110° | — | — | — |
| | 120° | 0.096 | 156 | 0.080 |
| 3 wk | 110° | 0.092 | 246 | 0.067 |
| | 120° | 0.091 | 219 | 0.069 |
| 6 wk | 110° | 0.087 | 359 | 0.051 |
| | 120° | 0.084 | 398 | 0.044 |
| 9 wk | 110° | 0.075 | 372 | 0.038 |
| | 120° | 0.069 | 417 | 0.027 |

These results show exceptional stability, far exceeding the results of prior art stable dentifrices which usually have a value of 0.060 after 3 weeks, whereas present rice hull dentifrice exceeds this value even after 9 weeks of accelerated aging.

Fluorine-containing compounds are an optionally preferred component in present rice hull dentifrice because of its beneficial effect on the care and hygiene of the oral cavity, e.g., diminution of enamel solubility in acid, and protection of the teeth against decay. Examples thereof include sodium fluoride, stannous fluoride, potassium fluoride, potassium stannous fluoride ($SnF_2KF$), sodium hexafluorostannate, stannous chlorofluoride, sodium fluorozirconate and sodium monofluorophosphate. These materials, which dissociate or release fluorine-containing ions in water, suitably may be present in an effective but non-toxic amount, usually within the range of about 0.01 to 1% by weight of the water soluble fluorine content thereof.

The rice hull dentifrices containing a fluorine compound have also been found to be non-corrosive. An unlined aluminum toothpaste tube containing the rice hull dentifrice of the present invention, and aged for 9 weeks at 120° F. was cut open and observed. No etchings or discolorations were evident.

It has also been found that anticaries activity of the rice hull dentifrice is retained after two months at room temperature in a suspended state, as evidenced by saliva glucose tests on 1 ml test solutions, using 3 ml saliva and 0.5 ml of 10% glucose solution.

The proportion of ground rice hulls, when used as the sole abrasive, may be as low as 18% and up to about 40%, preferably 36% by weight of the dentifrice to provide a toothpaste of suitable consistency. However, other conventional dental abrasives may be substituted for part of the ground rice hull abrasive in amounts of less than 50% of the total abrasive content. The total abrasive content is less than 50% and preferably does not exceed 40% by weight of the dentifrice. Suitable conventional dental abrasives have a Mohs hardness of less than 6 and a particle size of about 2–40 microns, and include hydrated alumina, anhydrous dicalcium phosphate, calcium pyrophosphate, insoluble sodium metaphosphate, dicalcium phosphate dihydrate, calcium carbonate, silica xerogels of the known high density or intermediate density types (such as those sold under the name Syloid 63 or Syloid 72 or Syloid 74), alkali metal or alkaline earth metal aluminosilicates (such as those having a refractive index of about 1.44–1.47, and containing at least about 70% silica, up to about 10% alumina, up to about 20% by weight of moisture and up to about 10% by weight of sodium oxide, the moisture content preferably being about 10–20% by weight, measured by loss at 1000° C., and the typical content of sodium oxide being about 5–10% by weight), kappa-alumina (such as described in U.S. Pat. No. 3,003,919); synthetic resins (such as described in British Pat. No. 995,351).

To make toothpastes or dental creams, the ground rice hulls and the other dental abrasives are dispersed in a dental vehicle which preferably contains a liquid which is water and/or a humectant such as glycerine, sorbitol, propylene glycol or polyethylene glycol 400 or 600, including suitable mixtures thereof. It is usually advantageous to use a mixture of both water and one or two humectants. The total liquid content is generally well over 20% by weight of the vehicle (sorbitol, generally present in admixture with water, is considered as a liquid for this purpose). The preferred humectants are glycerine and polyethylene glycol. Typically the vehicle contains about 10–80% by weight of glycerine, or other humectant, and about 5–80% of water.

The vehicle usually also contains a thickening or gelling agent, such as the natural and synthetic gums and gum-like materials, such as Irish Moss, gum tragacanth, alkali metal (e.g., Li, K or Na) carboxymethyl cellulose and hydroxymethyl carboxyethyl cellulose, polyvinyl pyrrolidone, starch, xanthan, water soluble hydrophilic colloidal carboxyvinyl polymers such as those sold under the trademark Carbopol 934 and 940, hydroxyethyl cellulose, Indian gum, acacia gums, agar agar, locust bean gum, Laponite CP or SP, which are each synthetic inorganic complex silicate clays sold under trademark by Laporte Industries, Ltd., and pectin or inorganic thickeners such as colloidal silica, e.g., synthetic finely divided silicas including those sold under the trademarks Cab-O-Sil M5, Syloid 244, Syloid 266 and Aerosil D200. The solid portion (thickening agent) of the vehicle is typically present in an amount up to about 11% by weight of the toothpaste, and as low as about 0.5% by weight.

The toothpaste may also contain surface active agent, e.g., to achieve increased prophylactic action, assist in achieving thorough and complete dispersion of the instant compositions throughout the oral cavity, and render the instant compositions more cosmetically acceptable. The organic surface active material may be anionic, nonionic, ampholytic, or cationic in nature, and it is preferred to employ as the surface active agent a detersive material which imparts to the composition detersive and foaming properties. Suitable types of such detergents are water soluble salts of higher fatty acid monoglyceride monosulfates, such as sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2 hydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl or N-palmitoyl sarcosine, which should be substantially free from soap or similar higher fatty acid material which tends to substantially reduce the effect of those compounds.

Other particularly suitable surface active materials include nonionic agents such as condensates of sorbitan monostearate with approximately 60 moles of ethylene oxide, condensates of ethylene oxide with propylene oxide condensates of propylene glycol ("Pluronics") and amphoteric agents such as quaternized imidazole derivatives, which are available under the trademark "Miranol" such as Miranol C₂M. Cationic surface active germicides and antibacterial compounds such as di-isobutylphenoxyethoxyethyl dimethyl benzyl ammonium chloride, benzyl dimethyl stearyl ammonium chloride, tertiary amines, having one fatty alkyl group (of from 12 to 18 carbon atoms) and two (poly) oxyethylene groups attached to the nitrogen (typically containing a total of from about 2 to 50 ethenoxy groups per molecule) and salts thereof with acids, and compounds of the structure:

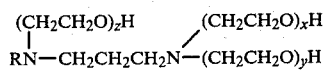

where R is a fatty alkyl group containing from about 12 to 18 carbon atoms, and x, y and z total 3 or higher, as well as salts thereof with mineral organic acids, may also be used. It is preferred that the total amount of surface active agent be about 0.5-5% by weight, preferably about 1-3%, of the dentifrice.

Various other materials may be incorporated in the oral preparation of this invention. Examples thereof are coloring or whitening agents, preservatives, silicones, chlorophyll compounds, ammoniated materials, such as urea, diammoniumphosphate and mixtures thereof, and other constituents. Each of these adjuvants may be typically incorporated in the instant toothpastes in amounts up to about 5%.

Suitable flavoring or sweetening sialagogues may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, sorbitol, sodium cyclamate and saccharin. Suitably, flavor and sweetening agent may together comprise from about 0.01 to 5% or more of the compositions of the instant invention.

The dentifrice may be prepared by suitably mixing the ingredients. For instance in making a toothpaste, a gelling agent such as sodium carboxymethyl cellulose or Carbopol 934 and a preservative such as sodium benzoate, if employed, is dispersed in a humectant such as glycerine. Water may also be present. Additional humectant and water may then be mixed with the dispersion and a homogeneous paste, gel or cream is formed. Dental abrasive agent, surface active agent and flavor are then added. The toothpaste is then thoroughly deaerated (e.g., in vacuo) and tubed. The formulation may be deaerated during mixing or after mixing. More specifically, the abrasive is added slowly and well blended into the paste, gel or cream until the abrasive is wet and foamy. Dry pockets of abrasive should be avoided.

Preferably the amount of water-insoluble essential oil flavoring oil is above 0.5% and below 2%. Strongly flavored toothpastes contain above 1% of such flavoring oil, e.g., about 1.2 to 1.5%.

The pH of the dentifrice is generally within the range of about 5 to 8.

DETAILED DESCRIPTION OF THE INVENTION

The following examples are given to illustrate this invention further. In this application all proportions are by weight unless otherwise indicated.

EXAMPLE 1

| Ingredient | % |
|---|---|
| Glycerine | 20.0 |
| Carboxymethyl cellulose-Na Salt | 1.0 |
| Sodium benzoate | 0.5 |
| Sodium Saccharin | 0.2 |
| Ground Rice Hulls (pass through 325 mesh) | 31.6 |
| Sodium lauryl sulfate | 1.5 |
| Flavor | 1.0 |
| Distilled Water | 44.2 |

A premix of carboxymethyl cellulose, saccharin, and benzoate dispersed in glycerine is prepared. The water is added to the premix and thoroughly mixed at high speed for about 20 minutes until a good vortex gel is formed. The abrasive is slowly added to said gel and well blended therewith until wet and foamy. This mixture is placed in a Ross mixer under vacuum and mixed at slow speed for 2 minutes and at increased speed for another 20 minutes. After reducing the mixing speed and breaking the vacuum, the sodium lauryl sulfate and flavor is blended with said formulation in the Ross mixer at high speed and under vacuum for about 10 minutes. The resultant product is a dentifrice formulation of suitable consistency. This toothpaste has a 32% stain removal value which is better than the 22% stain removal value of a commercial toothpaste containing 33% of a mixture of hydrated alumina, hydrated silica and dicalcium phosphate as dental abrasive.

EXAMPLE 2

| Ingredients | % |
| --- | --- |
| Glycerine | 15.6 |
| Carboxymethyl cellulose-Na Salt | 0.78 |
| Sodium Benzoate | 0.35 |
| Sodium Saccharin | 0.14 |
| Distilled Water | 45.86 |
| Ground Rice Hulls (pass through 325 mesh) | 35.5 |
| Sodium Lauryl Sulfate | 1.06 |
| Flavor | 0.71 |

The formulation is prepared in accordance with the procedure of Example 1.

This product exhibits very good toothpaste consistency even though less than 50% dental abrasive is used.

The pH of a 5% aqueous slurry is 6.23.

EXAMPLE 3

| Ingredients | % |
| --- | --- |
| Glycerine | 21.15 |
| Carboxymethyl cellulose Na Salt | 0.96 |
| Sodium Benzoate | 0.48 |
| Sodium Saccharin | 0.19 |
| $TiO_2$ | 0.38 |
| Distilled Water | 35.34 |
| Ground Rice Hulls (pass through 325 mesh) | 21.5 |
| Dicalcium phosphate | 17.6 |
| Sodium Lauryl Sulfate | 1.44 |
| Flavor | 0.96 |

This toothpaste is prepared in accordance with the procedure in Example 1.

A much lighter colored product is obtained of good toothpaste consistency.

EXAMPLE 4

| Ingredients | % |
| --- | --- |
| Polyethylene Glycol 600 | 55.10 |
| Distilled Water | 13.00 |
| Sodium Benzoate | 0.5 |
| Sodium Saccharin | 0.2 |
| Ground Rice Hulls (pass through 325 mesh) | 18.0 |
| Syloid 244[1] | 10.70 |
| Sodium Lauryl Sulfate | 1.5 |
| Flavor | 1.0 |

[1] Low density silica gel particles of about 4 micron average particle size

This toothpaste is prepared according to the procedure of Example 1.

The pH of a 5% aqueous slurry is 5.94.

This product has very good consistency but is dark brown in color.

EXAMPLE 5

Example 1 is repeated except that 0.76% sodium monofluorophosphate is added to the composition and the water content is reduced to 43.4% by weight. The monofluorophosphate is solubilized in the carboxymethyl cellulose prior to the addition of the water and the formation of a gel.

The resultant fluoride-containing dentifrice is of suitable consistency and has excellent cleaning and stain removal properties.

Other thickening or gelling agents can be substituted for the carboxymethyl cellulose or Syloid in the above examples such as hydroxyethyl cellulose and the like. Similarly, other conventional dental abrasives can replace the dicalcium phosphate abrasive such as calcium pyrophosphate, insoluble sodium metaphosphate and the like. Likewise, sodium lauryl sulfate may be replaced by other suitable surface active agents such as sodium dodecyl benzene sulfonate, N-lauroyl sarcosine, ethoxylated sorbitan monostearate, etc. Other fluorine-containing compounds can be substituted for the monofluorophosphate such as sodium fluoride, potassium fluoride, stannous fluoride and the like.

All of the dentifrices containing ground rice hulls having a particle size which pass 325 mesh have excellent cleaning and stain removal properties; are stable in the presence of a fluoride-containing compound and are non-corrosive. This dentifrice product containing less than 40% total dental abrasive of which the ground rice hulls constitutes more than half of the abrasive content, exhibits the necessary consistency required by conventional dentifrices containing 50% total abrasive.

It is understood that the foregoing detailed description is given merely by way of illustration and that variations may be made therein without departing from the spirit of the invention. The Abstract above is merely for the convenience of technical searchers and is not to be given any weight with respect to the scope of the invention.

We claim:
1. A dentifrice comprising, as the essential dental abrasive, ground rice hull particles which pass a 200 mesh sieve size, the total amount of abrasive constituting less than 40% by weight of the composition.
2. A dentifrice according to claim 1, wherein the ground rice hull particles pass a 325 mesh sieve size.
3. A dentifrice according to claim 1, also containing a dental abrasive having a particle size of about 2 to 40 microns and a Moh hardness of less than about 6, in an amount less than the ground rice hull content and less than 50% of the total abrasive content.
4. A dentifrice according to claim 3, wherein the additional abrasive is dicalcium phosphate.
5. A dentifrice according to claim 1, containing a fluorine-containing compound.
6. A dentifrice according to claim 5, wherein the fluorine compound is a monofluorophosphate.
7. A dentifrice according to claim 1, wherein the ground rice hulls is the sole dental abrasive in an amount of about 18–40% by weight of the composition.
8. A dentifrice according to claim 1, containing about 0.5–11% by weight of a gelling agent.
9. A dentifrice according to claim 8, wherein the gelling agent is an alkali metal carboxymethyl cellulose.
10. A dentifrice according to claim 8, containing about 0.05–5% by weight of a surface active agent.

* * * * *